United States Patent [19]

Bergink

[11] Patent Number: 5,236,913
[45] Date of Patent: Aug. 17, 1993

[54] 11-METHYLENE-OESTR-15-ENES, PROCESSES FOR THEIR PREPARATION, AND PHARMACEUTICAL COMPOSITIONS

[75] Inventor: Engelbert W. Bergink, Oss, Netherlands

[73] Assignee: Akzo N.V., Arnhem, Netherlands

[21] Appl. No.: 677,878

[22] Filed: Apr. 1, 1991

Related U.S. Application Data

[63] Continuation of Ser. No. 887,574, Jul. 17, 1986, abandoned.

[30] Foreign Application Priority Data

Jul. 24, 1985 [NL] Netherlands .................... 8502115

[51] Int. Cl.$^5$ ..................... A61K 31/56; C07J 7/00
[52] U.S. Cl. .................................. 514/179; 514/182; 552/526
[58] Field of Search ............... 552/526; 514/179, 182

[56] References Cited

U.S. PATENT DOCUMENTS 3,927,046  12/1975  van den Broek .................. 552/511

FOREIGN PATENT DOCUMENTS 051762  5/1982  European Pat. Off. .
7216767  6/1974  Netherlands .

OTHER PUBLICATIONS

Ralph I. Dorfman, "Androgens and anabolic agents. In Dorfman R. I.", *Methods in Hormone Research*, vol. II, Bioassay, Academic Press. Cover page. (1962).
C. W. Emmens, "Estrogens. In: Dorfman R. I." (ed) *Methods in Hormone Research*, vol. II, Bioassay, Academic Press. Page 65. (1962).
T. Miyake, "Progestational Substances In: Dorfman R. I." (ed) *Methods in Hormone Research*, vol. II, Bioassay. Academic Press, p. 135 (1962).
R.I. Dorfman, "Androgens and anabolic agents." In: Dorfman R. I. (ed), *Methods in Hormone Research*, vol. II Bioassay, Academic Press, pp. 304–305 (1962).
David J. Finney, "Assays based on quantal responses." In: *Statistical method in biological assay*. Third Edition. Charles Griffin & Company Ltd., p. 370.
A. J. van den Broeck, et al., "11-Aklylidene steroids in the 19-nor series", *Recueil, Journal of the Royal Netherlands Chemical Society*, vol. 94, No. 2, Feb. 1975, pp. 35–39.
L. Wiinikka et al., "Metabolism of a New Synthetic Progestagen, Org 2969, in Female Volunteers. Pharmacokinetics after an Oral Dose", *European Journal of Clinical Pharmacology*, vol. 15, pp. 349–355 (1979).
Lasse Viinikka, "Metabolism of a New Synthetic Progestagen, Org 2969, By Human Liver in Vitro", *Journal of Steroid Biochemistry*, vol. 10, pp. 353 to 357, (1979).

Primary Examiner—Marianne M. Cintins
Assistant Examiner—Rebecca Cook
Attorney, Agent, or Firm—Spencer, Frank & Schneider

[57] ABSTRACT

The present invention is concerned with novel 11-methylene-oestr-15-enes of the formula:

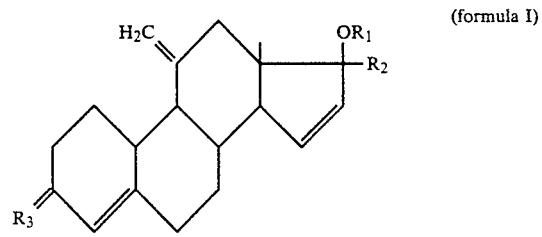

(formula I)

wherein
  $R_1$ = H or acyl with 1–18 C-atoms, preferably H,
  $R_2$ = ethinyl, vinyl, chloroethinyl, allyl or propinyl; ethinyl being preferred, and
  $R_3$ = O or $H_2$, preferably O.

Further the present invention is concerned with processes for the preparation of the above compounds and with pharmaceutical compositions comprising these compounds. The compounds possess powerful gestagenic properties and only slight androgenic side-effects.

5 Claims, No Drawings

11-METHYLENE-OESTR-15-ENES, PROCESSES FOR THEIR PREPARATION, AND PHARMACEUTICAL COMPOSITIONS

CROSS-REFERENCE TO RELATED APPLICATION

This is a continuation application of application Ser. No. 06/887,574 filed Jul. 17th, 1986, now abandoned, the entire specification of which is incorporated herein by reference.

The invention relates to 11-methylene-oestr-15-enes, to processes for their preparation and to pharmaceutical compositions which comprise these oestrenes.

The invention in particular relates to 11-methylene-oestra-4,15-dienes which possess an unsaturated hydrocarbon group in the 17α-position.

Such steroids are known. Thus, EP-A-0,051,762 describes 11-methylene-18-methyl-oestra-4,15-dien-3-ones which in the 17α-position are substituted by an ethinyl, chloroethinyl or propinyl group and additionally possess a 17β-OR$_1$ group, wherein R$_1$ represents H or an acyl group. These steroids possess powerful gestagenic properties and only slight androgenic side-effects.

A new group of 11-methylene-oestr-15-enes having valuable biological properties has now been found. These new 11-methylene-steroids have the general formula I:

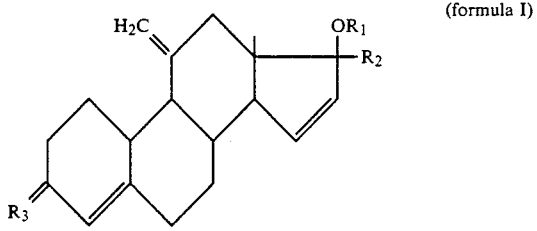
(formula I)

wherein
R$_1$=H or acyl with 1-18 C-atoms, preferably H,
R$_2$=ethinyl, vinyl, chloroethinyl, allyl or propinyl; ethinyl being preferred, and
R$_3$=O or H$_2$, preferably O.

The acyl group with 1-18 C-atoms can be derived from a saturated or unsaturated organic carboxylic acid. As examples of such carboxylic acids there may be mentioned formic acid, acetic acid, propionic acid, butyric acid, isobutyric acid, valeric acid, caproic acid, oenanthic acid, caprylic acid, pelargonic acid, capric acid, undecylic acid, lauric acid, tridecylic acid, myristic acid, pentadecylic acid, oleic acid, palmitic acid, stearic acid, adamantanecarboxylic acid, trimethylacetic acid, diethylacetic acid, cyclohexanecarboxylic acid, cyclopentylpropionic acid, cyclohexylbutyric acid, cyclohexylpropionic acid, undecylenic acid, benzoic acid, phenylacetic acid, phenylpropionic acid, phenylbutyric acid, phenoxyacetic acid, acetylacetic acid, malonic acid, succinic acid, glutaric acid, pimelic acid and tartaric acid.

The new compounds can be prepared in accordance with methods which are in themselves obvious. Usually, the starting materials are the corresponding 11-methylene-oestr-4-en-17-ones which are described in NL-A-7,216,767, and into these the double bond between C-15 and C-16 is introduced, after which the substituents in positions 3 and/or 17, if these are desired and not yet present, are introduced.

The double bond between C-15 and C-16 can be obtained by first introducing a 15α-hydroxyl group microbiologically into an 11-methylene-oestr-4-en-17-one compound then carrying out a dehydration reaction.

A 15α-hydroxylation can for example be effected with fungi of the genus Penicillium, for example *P. raistrickii* or *P. patulum*, or with species of the genera Colletotrichum, Giberella or Glomerella, for example *Colletotrichum antirrhini, Giberella baccata* or *Glomerella cingulata*.

The dehydration is advantageously carrier out by converting the 15α-hydroxyl group to the acylate or sulphonate, after which the 15α-acyloxy or 15α-sulphonyloxy group is split off, with formation of the double bond between C-15 and C-16.

Suitable acyl groups are acetyl, trifluoroacetyl, propionyl, butyryl, heptanoyl and benzoyl.

Suitable sulphonyl groups are mesyl, ethanesulphonyl, propionylsulphonyl and p-tosyl.

The esterification of the 15α-hydroxyl group is carried out in the usual manner by reacting with an acid, an acid anhydride or an acid chloride, in the presence of a strong acid, such as p-toluenesulphonic acid, or in the presence of a base, for example a tertiary amine, such as pyridine or 4-(dimethylamino)pyridine, if desired at an elevated temperature.

The sulphonylation is usually carried out with the appropriate sulphonyl chloride in an anhydrous medium, for example in dry pyridine, with the aid of dimethylformamide and sodium acetate.

The introduction of the substituent R$_2$ can be effected in the customary manner by alkylating the 17-oxo compound with an organo-metallic ethinyl, vinyl, chloroethinyl, allyl or propinyl compound.

Examples of such organo-metallic compounds are potassium acetylide, vinyl-magnesium bromide, lithium chloroacetylide, allylmagnesium bromide and potassium methylacetylide. The organo-metallic compound can also be formed in situ, after which it is reacted with the 17-ketone.

A 17α-vinyl compound can also be obtained by partial reduction of a 17α-ethinyl compound, for example with the aid of hydrogen in the presence of a catalyst, such as nickel, platinum or palladium on bariumsulphate.

During the introduction of the double bond between C-15 and C-16 a 3-oxo group which may be present is temporarily protected, in the customary manner, in the form of an acetal thereof, for example the acetal derived from ethylene glycol, ethanedithiol or 2,2-dimethyl-1,3-propanediol.

The cleavage of the acetal (in the case of a thioacetal, after activation) can be effected with acids, for example with sulphuric acid, perchloric acid, hydrochloric acid or oxalic acid, preferably in alcoholic solution or in acetone, if desired at an elevated temperature.

A 3-dithioethylenedithioacetal group which may be present can also be cleaved reductively, for example with sodium in ammonia or with lithium in methylamine, thereby giving a compound where R$_3$=H$_2$. In this reduction, a 17α-substituent having a triple bond, if present, is reduced to a substituent with a double bond, for example, 17α-ethinyl becomes 17α-vinyl. For the preparation of the 3-desoxo-17α-ethinyl compound it is also possible to start from a 3-desoxo-11-methylene-17-ketone.

Esterification of the 17β-hydroxyl group, if desired, can be effected in the customary manner, as described above for the 15α-hydroxyl group.

The new compounds according to the invention, especially 11-methylene-17α-ethinyl-17β-hydroxy-oestra-4,15-dien-3-one, possess improved ovulation-inhibiting properties upon oral administration in comparison with the -18-methyl analogues, described in EP-A-0,051,762. Further the new compounds are less androgenic than the corresponding 11-methylene compounds without a double bond between C-15 and C-16, described in NL-A-7,216,767. In particular, receptor binding studies with human cell lines show that 11-methylene-17α-ethinyl-17β-hydroxy-oestra-4,15-dien-3-one has a more advantageous profile than the corresponding known compounds. The very low affinity to SHBG (steroid hormone binding globulin) is also striking. It is believed that the lower affinity to SHBG reduces the metabolic burden of the liver.

Compared to the known 18-methyl compounds, they furthermore have the advantage that they are simpler to prepare. -18-Methyl-steroids are usually prepared by total synthesis. This complicated method of preparation, whereby racemates are produced, is not necessary for the preparation of the new compounds. Methods of preparation of 18methyl-steroids, wherein the 18-methyl group is introduced into 13-methyl-steroids, are also known, see, for example, NL-A-7,409,512 and NL-A-7,411,607. These reactions, too, need not be used in the preparation of the new steroids according to the invention.

The compounds according to the general formula I can, usually after having been mixed with auxiliaries and, if desired, with other active constituents, be administered parenterally or enterally, in the form of solutions, suspensions, emulsions or solid pharmaceutical mouldings, such as tablets, pills and dragees. They are especially suitable for use in contraceptive preparations, either by themselves or in combination with an oestragen, such as ethinyloestradiol, or an oestradiol-17β-ester, for example oestradiol-17β-valerate, oestradiol-17β-decanoate or oestradiol-17β-cyclooctylacetate.

For oral administration there are used, for example, tablets, containing 0.02-0.4 mg of a compound according to the general formula I and 0.02-0.05 mg of ethinyloestradiol (or an equivalent amount in respect of effect) of oestradiol-17β-ester), of which, for example, one tablet per day is taken.

The examples which follow illustrate the invention.

EXAMPLE 1 a) 11-Methylene-15α-hydroxy-oestr-4-ene-3,17-dione 50 ml of a medium consisting of a mixture of glucose (10 g/l) and yeast extract (10 g/l) were introduced into a 250 ml shaken Erlenmeyer flask. The medium was inoculated with spores of *Gomerella cingulata* (ATCC 10534). It was then incubated for 2 days at 28° C., with shaking.

The preculture thus obtained was used to inoculate 2 liters of medium (containing 40 g/l of glucose and 10 g/l of yeast extract) in a 5 liter fermenter). The mixture was incubated with stirring (750 rpm) at 28° C. at pH 5.0 for 16 hours, while passing air (0.2 liter/liter of medium/minute) through it. Thereafter, 11-methylene-oestr-4-ene-3,17-dione (0.6 g), suspended in 40 ml of Tween ® 80 (10%), was added.

After 25 hours, the reaction which was extracted with a 9/1 methylene chloride/methanol mixture. The extract was evaporated to dryness and the residue was purified by chromatography over silica gel and crystallization from methanol.

0.26 g of 11-methylene-15α-hydroxy-oestr-4-ene-3,17-dione was obtained, melting point 237° C. and $[\alpha]_D^{20} = +294$ (chloroform, c=1%).

b) 11-Methylene-oestra-4,15-diene-3,17-dione-3-ethylenedithioacetal 10.6 ml of ethanedithiol and 4.6 ml of boron trifluoride etherate were added successively, at 0°-5° C., to a cooled suspension of 21.3 g of 11-methylene-15α-hydroxy-oestr-4-ene-3,17-dione in 320 ml of methanol. After the reaction mixture had been stirred for 6 hours at 0°-5° C., it was poured out into 4.5 liters of water and the precipitate was filtered off, washed neutral with water and dried in vacuo.

The 26.7 g of crude 11-methylene-15α-hydroxy-oestr-4-ene-3,17-dione-3-ethylenedithioacetal, thus obtained, were employed in the next step without further purification. An analytical sample was obtained after crystallization from acetonitrile. Melting point 228° C.; $[\alpha]_D^{20} = +240$ (in cloroform, c=1%).

The crude product was dissolved in 172 ml of dry pyridine. 34.3 ml of methanesulphonyl chloride were added dropwise to this solution at 0°-5° C. over three quarters of an hour, with good stirring and in a nitrogen atmosphere. After 1.5 hours of stirring at 0°-5° C., 139.5 ml of dry dimethylformamide and 82.5 g of anhydrous sodium acetate were added. After this reaction mixture had been stirred for 5.5 hours at room temperature, it was poured out into 5 liters of water. The precipitate was filtered off, thoroughly washed with water and dried in vacuo. After purification by chromatography over silica gel followed by crystallisation from methylene dichloride/acetonitrile, 17.4 g of 11-methylene-oestra-4,15-diene-3,17-dione-3-ethylene-dithioacetal were obtained; melting point 207.5° C.; $[\alpha]_D^{20} = +142$ (chloroform; c=1%).

c) 11-Methylene-17α-ethinyl-17β-hydroxy-oestra-4,15-diene-3-one-3-ethylenedithioacetal A solution of 3.5 g of 11-methylene-oestr-4,15-diene-3,17-dione-3-ethylenedithioacetal in 52.5 ml of dry tetrahydrofuran was added, at −15° C. to −20° C., with stirring, to a tetrahydrofuran solution of potassium acetalide, prepared from 8.4 g of potassium tert.-butylate in acetylene. The reaction mixture was stirred for a further hour at this temperature, with continuous passage of acetylene. Thereafter, a mixture of 10 ml of water and 10 ml of tetrahydrofuran was added dropwise to the reaction mixture at −15° C. to −20° C. The reaction mixture was then poured out into a mixture of 1 liter of saturated NaCl solution and 0.5 liter of water. The precipitate was filtered off, washed neutral with water and dried in vacuo. After purification by chromatography over silica gel and crystallisation from diethyl ether/hexane, 2.6 g of 11-methylene-17α-ethinyl-17β-hydroxy-oestra-4,15-diene-3-one-3-ethylenedithioacetal were obtained, melting point 170.5° C.; $[\alpha]_D^{20} = -21$ (chloroform, c=1%).

d) 11-Methylene-17α-ethinyl-17β-hydroxy-oestra-4,15-diene-3-one 1.41 g of potassium carbonate and 8.1 ml of methyl iodide were added successively to a suspension of 3 g of the dithioacetal of Example Ic) in a mixture of 76 ml of methanol and 5 ml of water. The reaction mixture was boiled for 20 hours under reflux, evaporated in vacuo to about 25 ml, further diluted with 250 ml of water and extracted with methylene chloride. The crude product was purified by chromatography over silica gel. Crystallisation of the pure fractions from hexane gave 1.5 g of 11-methylene-17α-ethinyl-17β-hydroxy-oestra-4, 15-diene-3-one; melting point 157° C., $[\alpha]_D^{20} = -44$ (chloroform, c=1%).

EXAMPLE II a) 11-Methylene-oestra-4,15-diene-3,17-dione-3-ethylene-dithioacetal-17-ethylenediacetal A solution of 15 g of 11-methylene-oestra-4,15-diene-3,17-dione-3-ethylenedithioacetal and 0.5 g p-toluene-sulphonic acid in 160 ml of methylene chloride, 320 ml of ethylene glycol and 48 ml of triethylorthoformate was boiled for 4 hours under a reflux condenser. Working up of the reaction mixture by extraction gave 16.9 g of 11-methylene-oestra-4,15-diene-3,17-dione-3-ethylenedithioacetal-17-ethylenediacetal.

b) 11-Methylene-oestra-4,15-diene-17-one-17-ethylenediacetal

A solution of 14 g of 11-methylene-oestra-4,15-diene-3,17-dione-3-ethylenedithioacetal-17-ethylenediacetal was added dropwise to a solution of 7.2 g of sodium in 280 ml of liquid ammonia in 30 minutes at −40° C., after which the mixture was stirred for a further 30 minutes at the same temperature. After working up and chromatography over silica gel, 9.2 g of 11-methylene-oestra-4,15-diene-17-one-17-ethylenediacetal were obtained.

c) 11-Methylene-oestra-4,15-diene-17-one

A solution of 8.8 g of 11-methylene-oestra-4,15-diene-17-one-17-ethylenediacetal in 175 ml of acetone and 0.9 of concentrated HCl was stirred for 1.5 hours at room temperature under N₂. Working up by extraction and crystallisation from ether gave 6.5 g of 11-methylene-oestra-4,15-diene-17-one.

d) 11-Methylene-17α-ethinyl-oestra-4,15-diene-17β-ol 6 g of 11-methylene-oestra-4,15-diene-17-one were ethinylated in the manner described in Example Ic), giving 2.1 g of 11-Methylene-17α-ethinyl-oestra-4,15-diene-17β-ol.

EXAMPLE III

11-Methylene-17α-ethinyl-oestra-4,15-diene-17β-ol

Following the procedure described in Example I and starting from 11-methylene-oestra-4-en-17-one 11-methylene-17α-ethinyl-oestra-4,15-diene-17β-ol was prepared, it being possible to omit the protection and deprotection of the 3-oxo group.

EXAMPLE IV

11-Methylene-17α-allyl-17β-hydroxy-oestra-4,15-diene-3-one

On repeating Example I with the difference that alkylation was carried out with allyl-magnesium bromide in Example Ic), 11-methylene-17α-allyl-17β-hydroxy-oestra-4,15-diene-3-one was obtained.

EXAMPLE V

11-Methylene-17α-(1-propinyl)-17β-hydroxy-oestra-4,15-diene-3-one

On repeating Example I with the difference that in Example Ic) alkylation was carried out with methylacetylene in the presence of butyl-lithium, 11-methylene-17α-(1-propinyl)-17β-hydroxy-oestra-4,15-diene-3-one was obtained.

EXAMPLE VI

11-Methylene-17α-chloroethinyl-17β-hydroxy-oestra-4,15-diene-3-one

On repeating Example I with the difference that in Example Ic) alkylation was carried out with 1,2-dichloroethylene in diethyl ether/ tetrahydrofuran (8:1), in the presence of methyl-lithium, 11-methylene-17α-chloroethinyl-17β-hydroxy-oestra-4,15-diene-3-one was obtained.

EXAMPLE VII

11-Methylene-17α-ethinyl-17β-hydroxy-oestra-4,15-diene-3-one-17β-acetate 1.8 g of 11-ethylene-17α-ethinyl-17β-hydroxy-oestra-4,15-diene-3-one were reacted at room temperature with 10 ml of acetic anhydride in 15 ml of pyridine in the presence of 150 mg of 4-dimethylaminopyridine. After 5 hours, the mixture was poured out into ice water and worked up. Chromatography of the product over silical gel, with acetone/hexane, gave 1.6 g of 11-methylene-17α-ethinyl-17β-hydroxy-oestra-4,15-diene-3-one-17β-acetate.

The 17β-esters derived from butyric acid, valeric acid and decylic acid were prepared analogously.

Description of Table

Measurements of binding affinities of 11-methylene-17α-ethinyl-17β-hydroxy-oestra-4,15-diene-3-one and the analogues with 18-methyl or without the double bond at position 15 to the progesteron-,the androgen- and the SHBG receptor revealed the following:

| compound | | receptor affinity to | | |
| --- | --- | --- | --- | --- |
| $\Delta^{15}$ | 18-CH₃ | progesteron receptor (3-keto desogestrel = 100) | androgen receptor (5α-dihydro testosterone = 100) | SHBG receptor (5α-DHT = 100) |
| + | − | 114 | 2 | 1 |
| − | − | 80 | 7 | 3 |
| + | + | 99 | 2 | 5 |

I claim:

1. An 11-methylene-steroid of the formula I:

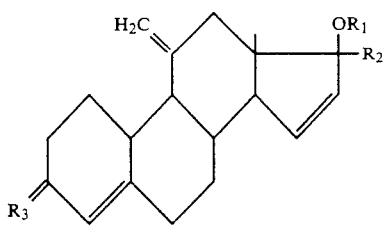 (formula I)
wherein
R₁=H,
R₂=ethinyl and
R₃=O or H₂.
2. Compound according to claim 1, wherein R₃=O.
3. The compound according to claim 1, 11-Methylene-17α-ethinyl-17β-hydroxy-oestra-4,15-diene-3-one.
4. A pharmaceutical preparation comprising at least one steroid according to claim 1 and a pharmaceutically acceptable auxiliary.
5. A compound according to claim 1 wherein R₃=H₂.
* * * * *